[19] United States Patent
Sarantakis

[11] 3,933,784
[45] Jan. 20, 1976

[54] DES-(SER¹³)-SRIF AND INTERMEDIATES
[75] Inventor: Dimitrios Sarantakis, Chester, Pa.
[73] Assignee: American Home Products Corporation, New York, N.Y.
[22] Filed: Jan. 27, 1975
[21] Appl. No.: 544,252

[52] U.S. Cl............................ 260/112.5 R; 424/177
[51] Int. Cl.²................. C07C 103/52; A61K 37/00
[58] Field of Search ............................ 260/112.5 R

[56] References Cited
UNITED STATES PATENTS

| | | |
|---|---|---|
| 3,842,066 | 10/1974 | McKinley et al............. 260/112.5 R |
| 3,842,067 | 10/1974 | Sarantakis.................... 260/112.5 R |
| 3,882,098 | 5/1975 | Sarantakis.................... 260/112.5 R |

Primary Examiner—Lewis Gotts
Assistant Examiner—Reginald J. Suyat

[57] ABSTRACT

The tridecapeptide H-Ala-Gly-Cys-Lys-Asn-Phe-Phe-Trp-Lys-Thr-Phe-Thr-Cys-OH, its oxidized form and intermediates obtained in such synthesis are described. This tridecapeptide inhibits the secretion of the hormone somatotropin (growth hormone).

6 Claims, No Drawings

DES-(SER¹³)-SRIF AND INTERMEDIATES

This invention relates to novel tridecapeptides and intermediates obtained in their synthesis by the solid phase method of peptide synthesis.

Somatostatin (also known as somatotropin release inhibiting factor or SRIF) is the tetradecapeptide

This tetradecapeptide has only recently been identified by isolation from extracts of ovine hypothalamic tissues and found to inhibit the secretion of the hormone somatotropin which is commonly referred to as the growth hormone (GH); See Brazeau et al., Science, 179 pp 77–79 (January 1973). The linear form of this tetradecapeptide, H-Ala-Gly-Cys-Lys-Asn-Phe-Phe-Trp-Lys-Thr-Phe-Thr-Ser-Cys-OH, has also been reported by Brazeau et al., supra, to have been synthesized by solid phase methodology and found to have the same biological activity as the somatostatin obtained from a natural source. In copending application Ser. No. 430,441 filed Jan. 3, 1974, now U.S. Pat. No. 3,882,098, the undecapeptide Des-Ala¹-Gly²-Asn⁵-SRIF and its oxidized form are described and in copending application Ser. No. 457,038 filed Apr. 1, 1974, the dodecapeptide Des-Ala¹-Gly²-SRIF and its oxidized form are described.

The novel tridecapeptides of the present invention are analogs of somatostatin and the linear counterpart of somatostatin in which the amino acid in the thirteen position of somatostatin has been omitted.

The tridecapeptide of the present invention which inhibits the secretion of the hormone somatotropin is represented by the formula:

(I-cyclic or oxidized form)

and the non-toxic acid addition salts thereof. Illustrative of acid addition salts are hydrochloride, hydrobromide, sulfate, phosphate, maleate, acetate, citrate, benzoate, succinate, malate, ascorbate and the like.

The nomenclature used to depict the peptides follows that described by Schroder & Lubke, "The Peptides," 1 pp viii-xxix (Academic Press 1965). All chiral amino acid residues identified in formulas I and II, supra, and the other formulas hereinafter are of the natural or L-configuration unless specified otherwise.

The present invention also relates to novel tridecapeptides intermediates of the formulas:

H-Ala-Gly-Cys-Lys-Asn-Phe-Phe-Trp-Lys-Thr-Phe-Thr-Cys-OH (II-linear form)

and   R-Ala-Gly-Cys(R¹)-Lys(R⁶)-Asn-Phe-Phe-Trp-Lys(R²)-Thr(R³)-Phe-Thr(R⁴)-Cys(R⁵)-X (III)

wherein:

R is either hydrogen or an α-amino protecting group. The α-amino protecting groups contemplated by R are those known to be useful in the art in the step-wise synthesis of polypeptides. Among the classes of α-amino protecting groups covered by R are (1) acyl type protecting groups illustrated by the following: formyl, trifluoroacetyl, phthalyl, toluenesulfonyl (tosyl), benzenesulfonyl, nitrophenylsulfenyl, tritylsulfenyl, o-nitrophenoxyacetyl, chloroacetyl, acetyl, γ-chlorobutyryl, etc.; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethan protecting groups illustrated by tert-butyloxycarbonyl, diisopropylmethoxycarbonyl, isopropyloxycarbonyl, ethoxycarbonyl, allyloxycarbonyl; (4) cycloalkyl urethan type protecting groups illustrated by cyclopentyloxycarbonyl, adamantyloxycarbonyl, cyclohexyloxycarbonyl; (5) thio urethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting group defined by R is tert-butyloxycarbonyl;

R¹ and R⁵ are a protecting group for the sulfhydryl group on the cysteinyl amino acid residue in the tridecapeptide. Illustrative of R¹ and R⁵ is a group selected from the class consisting of benzyl; substituted benzyl wherein the substituent is at least one of methyl, methoxy, nitro (e.g. p-methylbenzyl, p-nitrobenzyl, 2,4,6-trimethylbenzyl, etc); carboxymethyl; trityl, benzyloxycarbonyl, benzhydryl, p-methoxybenzyloxycarbonyl, benzylthiomethyl, ethylcarbamyl, thioethyl, tetrahydropyranyl, acetamidomethyl, benzoyl, s-sulfonate salt, etc.

R² and R⁶ are a protecting group for the side chain amino substituent of lysine or R² and/or R⁶ is hydrogen which means there is no protecting group on the side chain amino substituent. Illustrative of suitable side chain amino protecting groups are benzyloxycarbonyl, substituted benzyloxycarbonyl, tosyl, t-amyloxycarbonyl, t-butyloxycarbonyl, diisopropylmethyloxycarbonyl, etc. The substituent on benzyloxycarbonyl may be halo (e.g. chloro, bromo, fluoro) or nitro (e.g. 2-chlorobenzyloxycarbonyl, p-nitrobenzyloxycarbonyl, 3,4-dichlorobenzyloxycarbonyl. The selection of such a side chain amino protecting group is not critical except that it must be one which is not removed during cleavage of the α-amino protecting group during the synthesis until the peptide of the desired amino acid sequence is obtained. Hence, the α-amino protecting and side chain amino protecting group should not be the same;

R³ and R⁴ are protecting groups for the alcoholic hydroxyl group of threonine and is selected from the class consisting of acetyl, benzoyl, tert-butyl, trityl, benzyl, 2,6 dichlorobenzyl and benzyloxycarbonyl. The preferred protecting group is benzyl; or R³, and/or R⁴ is hydrogen which means there is no protecting group on the alcoholic hydroxyl function.

X is selected from the class consisting of OH, OCH₃ and an anchoring bond used in solid phase synthesis linked to a solid resin support represented by the formula —O—CH₂—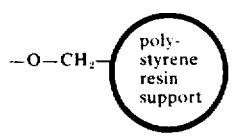

The polystyrene resin support is preferably a copolymer of styrene with about 1 to 2% divinyl benzene as a cross linking agent which causes the polystyrene polymer to be completely insoluble in certain organic solvents. The polystyrene polymer is composed of long alkyl chains bearing a phenyl ring on every second carbon and the terminal amino acid residue (Cys) is joined through a covalent carbon to carbon bond to these phenyl rings. The alkyl chains are cross linked at approximately every fiftieth carbon by p-diethylphenyl residues derived from divinyl benzene.

In selecting a particular $R^1$, $R^2$, $R^3$, $R^4$, $R^5$ and $R^6$ side chain protecting group to be used in the synthesis of the peptides of formula (III), the following rules should be followed: (a) the protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The tridecapeptide peptide of formula (I) is prepared using solid phase synthesis. The synthesis is commenced from the C-terminal end of the peptide using an α-amino protected resin. Such a starting material can be prepared by attaching an α-amino protected cysteine to a chloromethylated resin or a hydroxymethyl resin. The preparation of the hydroxymethyl resin is described by Bodanszky et al., Chem. Ind. (London) 33, 1597–98 (1966). A chloromethylated resin is commercially available from Bio Rad Laboratories Richmond, California and the preparation of such a resin is described by Stewart et al., "Solid Phase Peptide Synthesis" (Freeman & Co., San Francisco 1969), Chapter 1, pp 1–6. The α-amino and sulfhydryl protected cysteine is coupled to the chloromethylated resin according to the procedure of Gisin, Helv. 56 p 1476 (1973). Following the coupling of the α-amino and sulfhydryl protected cysteine to the resin support, the α-amino protecting group is removed such as by using trifluoroacetic acid in methylene chloride, trifluoroacetic acid alone or HCl in dioxane. The deprotection is carried out at a temperature between about 0°C and room temperature. Other standard cleaving reagents and conditions for removal of specific α-amino protecting groups may be used as described in Schroder & Lubke, supra, 1 pp. 72–75. After removal of the α-amino protecting group the remaining α-amino protected amino acids are coupled step-wise in the desired order to obtain a compound of formula (II) or as an alternate to adding each amino acid separately to the synthesis, some of them may be coupled prior to addition to the solid phase reactor. The selection of an appropriate coupling reagent is within the skill of the art. A particularly suitable coupling reagent is N,N¹-diisopropyl carbodiimide. As previously indicated, the activating reagents used in the aforedescribed synthesis are those well known in the peptide art. Illustrative of these are (1) carbodiimides (e.g. N,N¹-dicyclohexylcarbodiimide, N-ethyl N¹-(γ-dimethylamino propyl carbodiimide); (2) cyanamides (e.g. N,N-dibenzylcyanamide; (3) ketenimines; (4) isoxazolium salts (e.g. N-ethyl-5-phenyl isoxazolium-3¹-sulfonate; (5) monocyclic nitrogen containing heterocyclic amides of aromatic character containing one through four nitrogens in the ring such as imidazolides, pyrazolides, 1,2,4-triazolides. Specific heterocyclic amides that are useful include N,N¹-carbonyl diimidazole, N,N¹-carbonyl-di-1,2,4-triazole; (6) alkoxylated acetylene (e.g. ethoxyacetylene); (7) reagents which form a mixed anhydride with the carboxyl moiety of the amino acid (e.g. ethylchloroformate, isobutylchloroformate) and (8) nitrogencontaining heterocyclic compounds having a hydroxy group on one ring nitrogen (e.g. N-hydroxyphthalimide, N-hydroxysuccinimide, 1-hydroxybenzotriazole). Other activating reagents and their use in peptide coupling are described by Schroder & Lubke supra, in Chapter III and by Kapoor, J. Pharm. Sci., 59, pp 1–27, (1970).

Each protected amino acid or amino acid sequence is introduced into the solid phase reactor in about a fourfold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser et al., Analyt. Biochem, 34, 595 (1970).

After the desired amino acid sequence of formula III has been synthesized, the peptide is removed from the resin support by treatment with a reagent such as liquid hydrogen fluoride which not only cleaves the peptide from the resin but also cleaves all remaining side chain protecting groups $R^1$, $R^2$, $R^3$, $R^4$, $R^5$ and $R^6$ and the α-amino protecting group R on alanyl to obtain a compound of formula II. As an alternate route, the tridecapeptide linked to the resin support may be separated from the resin by methanolysis after which the recovered C-terminal methyl ester is converted to the acid by hydrolysis. Any side chain protecting group may then be cleaved as previously described or by other procedures such as catalytic reduction (e.g. Pd on BaSO₄) using conditions which will keep the Trp moiety intact.

When using hydrogen fluoride for cleaving, anisole is included in the reaction vessel to prevent the oxidation of labile amino acid (e.g. tryptophan). The tridecapeptide of formula II is converted to the tridecapeptide of formula I by air oxidation, preferably by surface oxidation as described in Example 2 herein.

The solid phase synthesis procedure discussed supra is well known in the art and has been essentially described by Merrifield J. Am. Chem. Soc., 85, p 2149 (1964).

The following examples are illustrative of the preparation of the compounds of formulas I through III.

EXAMPLE 1 t-Butyloxycarbonyl-L-alanylglycyl-S-p-methoxybenzyl-L-cysteinyl-N$^\epsilon$-2-chlorobenzyloxycarbonyl-L-lysyl-L-asparaginyl-L-phenylalanyl-L-phenylalanyl-L-tryptophyl-N$^\epsilon$-2-chlorobenzyloxycarbonyl-L-lysyl-O-benzyl-L-threonyl-L-phenylalanyl-O-benzyl-L-threonyl-S-3,4-dimethylbenzyl-L-cysteinyl; hydroxy methylated polystyrene resin A solution of the cesium salt of t-Boc-S-3,4-dimethylbenzyl-L-cysteine (25 m moles) in dimethylformamide is stirred with chloromethylated polystyrene resin (30 g) at 50°C in a pressure bottle for 16 hours. The resin is filtered and washed with dimethylformamide, 10% water in dimethylformamide, ethanol and dimethylformamide (1:1), dimethylformamide, methylene chloride, and methanol. The resin, after drying in vacuo over potassium hydroxide, is found to be substituted to the extent of 0.40 m moles of cysteine per gram of resin.

Five grams of this resin is transferred to a solid phase reaction vessel and using the following sequence of deprotection, neutralization, and coupling steps the above titled compound is prepared:

Deprotection a. 2 treatments for twenty minutes each with 30% trifluoroacetic acid in methylene chloride containing 0.5% dithioerythritol; b) methylene chloride wash; c) dimethylformamide wash.

Neutralization a. 2 treatments for three minutes each with 15% triethylamine in dimethylformamide; b) dimethylformamide wash (2 times); c) methylene chloride wash (5 times).

coupling

A 10% excess of diisopropylcarbodiimide is used for each coupling which is effected two times for a total of 20 hours before initiating the next deprotection, neutralization, and coupling cycle. All couplings are carried out at ambient temperature in 3:1 methylene chloride and dimethylformamide. The only exception is t-Boc-L-asparagine which is coupled via its trichlorophenyl ester for a total of 3 days in 1:1 dimethylformamide and dimethylacetamide.

The following amino acid residues are introduced consecutively: t-Boc-O-benzyl-L-threonine (3 m moles), t-Boc-L-phenylalanine (3 m moles), t-Boc-O-benzyl-L-threonine (3 m moles), t-Boc-N$^\epsilon$-(2-chlorocarbobenzoxy)-L-lysine (3m moles), t-Boc-L-tryptophan (3 m moles), t-Boc-L-phenylalanine (3 m moles), t-Boc-L-phenylalanine (3 m moles), t-Boc-L-asparagine trichlorophenyl ester (6 m moles), t-Boc-N$^\epsilon$-(2-chlorobenzyloxycarbonyl)-L-lysine (3 m moles), t-Boc-S-methoxybenzyl-L-cysteine (3 m moles), and t-Boc-L-alanylglycine (3 m moles).

The washed resin is dried in vacuo overnight.

EXAMPLE 2

L-Alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-cysteine-(3-13 cyclic)disulfide The above described preparation obtained in Example 1 is treated in vacuo with liquid anhydrous hydrogen fluoride (50 ml) and anisole (10 ml) at ambient temperature for 45 minutes. The hydrogen fluoride is removed as quickly as possible under reduced pressure, and the residue is washed with ether, this residue being the compound of formula II. The remaining residue is extracted with 1 N acetic acid (flushed with nitrogen), the combined extracts are diluted with water flushed with nitrogen, to 4500 ml and the pH adjusted to 7.8 with dilute NH$_4$OH. After standing in the open air for 48 hours the solution is lyophilized to a powder (2.84 g) which is the above-titled compound.

EXAMPLE 3

Purification and characterization of L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-cysteine-(3-13 cyclic) disulfide The above crude product from Example 2 is purified as follows:

2.84 g of this product is 5 ml of the upper phase of n-butanol: water: acetic acid (4:5:1) is applied to the top of a column (2.9 cm in diameter and 150 cm in height) with a bed of Sephadex G-25 medium previously equilibrated with first the lower phase of that system and then the upper phase. The column is eluted with the upper phase and fractions of 4 ml each are taken. Analysis of the column effluent is carried out by use of the Folin-Lowry color reaction on every third fraction. Seven main peptide containing fractions are obtained: A) 65–110 (220 mg), B) 111–145 (208 mg), C) 146–165 (102 mg), D) 166–180 (170 mg), E) 181–200 (338 mg), F) 201–215 (159 mg), G) 216–250 (126 mg). Fraction E is shown by thin layer chromatography systems BWA (4:1:1) (n-butanol: water: acetic acid) on cellulose and BWAP (4:2:1:1) (n-butanol water: acetic acid: pyridine) in silica gel to be nearly homogenous. Fraction E is applied in 2 ml. of 1 N acetic acid to the top of a column (2.9 cm in diameter and 150 cm in height) with a bed of Sephadex G-25 fine previously equilibrated with 1 N acetic acid and eluted with that solvent. Fractions of 3 ml each are taken and the effluent is monitored as described before. Three main peptide containing fractions are obtained: A) 169–183 (64 mg), B) 184–190 (116 mg), C) 191–197 (62 mg). Fraction B is homogenous by the thin layer chromatography systems described previously (BWAP 4:2:1:1 on silica gel R$_f$ 0.42 and BWA 4:1:1 on cellulose R$_f$ 0.48). Thin layer chromatograms are visualized by chlorine peptide reagent. $[\alpha]_D^{25} = -35.3$ (c – 0.99, 1% AcOH).

After hydrolysis of the peptide in methanesulfonic acid for 18 hours at 120°C in an evacuated sealed tube, the following values for the amino acid residues are obtained: Ala 1.00, Gly 1.00, Cys 1.59, Lys 1.88, Asp 0.99, Phe 3.05, Trp (present, but not quantitated), Thr 1.76. The growth hormone activity of the compound of Example 3 was determined by injecting rats weighing about 200–250 g first with nembutal intraperitoneally at a dose of 50 mg/kg then after 5 minutes injecting the rats subcutaneously with a solution of the compound of Example 3 in saline at a dose of 800 μg per rat. Blood samples are taken 15 minutes after injection with the compound of Example 3 and the growth hormone level determined by radioimmunoassay. The average growth hormone level in the control rats (7 animals) was found to be 159 ± 16 ng/ml whereas the growth hormone level in the rats (8 animals) given the compound of Example 3 was found to be 49 ± 7 ng/ml.

The compounds of formula I described herein may be administered to warm blooded mammals, including humans, either intravenously, subcutaneously, intramuscularly or orally to inhibit the release of growth hormone where the host being treated requires therapeutic treatment for excess secretion of somatotropin which is associated with conditions such as juvenile diabetes and acromegaly. The contemplated dose range for oral administration in tablet or capsule form to large mammals is about 0.015 mg to about 7 mg/kg of body weight per day while the dose range for intravenous injection in an aqueous solution is about 0.14 µg to about 0.15 mg/kg of body weight per day. When administered subcutaneously or intramuscularly a dose range of about 1.5 µg to about 7 mg/kg of body weight per day is contemplated. Obviously, the required dosage will vary with the particular condition being treated, the severity of the condition and the duration of treatment.

If the active ingredient is administered in tablet form the tablet may contain: a binder such as gum tragacanth, corn starch, gelatin, an excipient such as dicalcium phosphate; a disintegrating agent such as corn starch, alginic acid, etc.; a lubricant agent such as sucrose, lactose, wintergreen, etc. Suitable liquid carriers for intravenous administration include isotonic saline, phosphate buffer solutions, etc.

What is claimed is:

1. A tridecapeptide selected from those of the formula

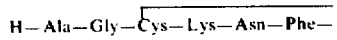

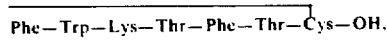

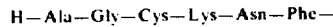

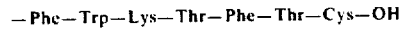

and the non-toxic acid addition salts thereof, said amino acid residues in said tridecapeptide having an asymmetric α-carbon atom being of the L-configuration.

2. A peptide according to claim 1 which is: L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-cysteine and a non-toxic acid addition salt thereof.

3. A peptide according to claim 1 which is: L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-cysteine (cyclic 1, 13 disulfide) and a non-toxic acid addition salt thereof.

4. A tridecapeptide of the formula:

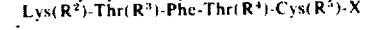

wherein:

R is selected from the group consisting of hydrogen and an α-amino protecting group;

$R^1$ and $R^5$ are protecting groups for the sulfhydryl group on the cysteinyl amino acid residue selected from the group consisting of benzyl, trityl, benzyloxycarbonyl, benzhydryl, tetrahydropyranyl, acetamidomethyl, benzoyl, benzylthiomethyl, ethylcarbamyl, thioethyl, p-methoxybenzyloxycarbonyl, s-sulfonate salt and substituted benzyl wherein said substituent is selected from the group consisting of methyl, methoxy and nitro;

$R^2$ and $R^6$ are selected from the group consisting of hydrogen and a protecting group for the side chain amino substituent of the lysine residue selected from benzyloxycarbonyl, tosyl, diisopropylmethyloxycarbonyl, t-amyloxycarbonyl, t-butyloxycarbonyl and substituted benzyloxycarbonyl wherein said substituent is selected from halo and nitro;

$R^3$ and $R^4$ are selected from the group consisting of hydrogen and a protecting group for the alcoholic hydroxyl group of the threonine residue selected from acetyl, benzoyl, tert-butyl, trityl, benzyl, 2,6-dichlorobenzyl and benzyloxycarbonyl;

X is selected from the class consisting of hydroxy, methoxy and

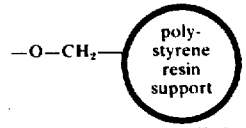

wherein said polystyrene is cross linked through the phenyl group on each second carbon atom of the alkyl chain of said polystyrene.

5. A compound according to claim 4 wherein R is tert-butyloxycarbonyl.

6. A compound according to claim 5 wherein: $R^1$ is pmethoxybenzyl; $R^2$ and $R^6$ are 2-chlorobenzyloxycarbonyl; $R^3$ and $R^4$ are each benzyl and $R^5$ is 3,4-dimethylbenzyl.

* * * * *